(12) United States Patent
Madabhushi et al.

(10) Patent No.: US 10,127,660 B2
(45) Date of Patent: Nov. 13, 2018

(54) RADIOMIC FEATURES ON DIAGNOSTIC MAGNETIC RESONANCE ENTEROGRAPHY

(71) Applicant: Case Western Reserve University, Cleveland, OH (US)

(72) Inventors: Anant Madabhushi, Shaker Heights, OH (US); Cheng Lu, Cleveland Heights, OH (US); Satish Viswanath, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 26 days.

(21) Appl. No.: 15/361,885

(22) Filed: Nov. 28, 2016

(65) Prior Publication Data
US 2017/0193655 A1 Jul. 6, 2017

Related U.S. Application Data

(60) Provisional application No. 62/272,762, filed on Dec. 30, 2015.

(51) Int. Cl.
*G06T 7/00* (2017.01)
*G06T 7/11* (2017.01)
*A61B 5/00* (2006.01)

(52) U.S. Cl.
CPC .......... *G06T 7/0012* (2013.01); *G06T 7/0081* (2013.01); *A61B 5/4255* (2013.01);
(Continued)

(58) Field of Classification Search
CPC .............. G06T 7/0012; G06T 7/0081; G06T 2207/10088; G06T 7/11;
(Continued)

(56) References Cited

U.S. PATENT DOCUMENTS 9,483,822 B2    11/2016  Madabhushi et al.
9,732,385 B2 *   8/2017  Barken ................ C12Q 1/6883
(Continued)

OTHER PUBLICATIONS

Mahapatra et al. "Automatic Detection and Segmentation of Crohn's Disease Tissues From Abdominal MRI." IEEE Transactions on Medical Imaging, vol. 32, No. 12, Dec. 2013, pp. 2332-2347.*
Lapidus, et al. "Clinical Course of Colorectal Crohn's Disease: A 35-Year Follow-up Study of 507 Patients." Gastroenterology, 114 (1998) 1151-1160.
(Continued)

*Primary Examiner* — Jon Chang
(74) *Attorney, Agent, or Firm* — Eschweiler & Potashnik, LLC

(57) ABSTRACT

Methods, apparatus, and other embodiments associated with predicting Crohn's Disease (CD) patient response to immunosuppressive (IS) therapy using radiomic features extracted from diagnostic magnetic resonance enterography (MRE). One example apparatus includes an image acquisition circuit that acquires an MRE image of a region of tissue demonstrating CD pathology, a segmentation circuit that segments a region of interest (ROI) from the diagnostic radiological image, a classification circuit that extracts a set of discriminative features from the ROI and that distinguishes the ROI as a responder or non-responder to IS therapy, and a CD prediction circuit that generates a radiomic enterographic (RET) score based on the diagnostic radiological image or the set of discriminative features. A prognosis or treatment plan may be provided based on the RET score.

20 Claims, 6 Drawing Sheets

(52) U.S. Cl.
CPC ....... *G06T 7/11* (2017.01); *G06T 2207/10088* (2013.01); *G06T 2207/30028* (2013.01)

(58) Field of Classification Search
CPC .......... G06T 2207/30028; A61B 5/055; A61B 5/4255; A61B 6/50; A61B 6/52
See application file for complete search history.

(56) References Cited

U.S. PATENT DOCUMENTS

| | | | | |
|---|---|---|---|---|
| 2011/0103657 | A1* | 5/2011 | Kang | G06K 9/6215 382/128 |
| 2012/0189176 | A1* | 7/2012 | Giger | G06K 9/6253 382/128 |
| 2015/0087957 | A1* | 3/2015 | Liu | G06T 7/42 600/408 |
| 2015/0310632 | A1* | 10/2015 | Banerjee | G06K 9/6267 382/131 |
| 2016/0203599 | A1* | 7/2016 | Gillies | A61B 6/463 382/132 |
| 2016/0210748 | A1* | 7/2016 | Nolte | G02B 21/14 |
| 2017/0193660 | A1* | 7/2017 | Schmidt | G06T 7/0012 |

OTHER PUBLICATIONS

Reyes-Aldasoro, et al. "The Bhattacharyya Space for Feature Selection and Its Application to Texture Segmentation." Pattern Recognition, 39 (2006) 812-826.

Viswanath, et al. "Identifying Quantitative in Vivo Multi-Parametric MRI Features for Treatment Related Changes After Laser Interstitial Thermal Therapy of Prostate Cancer." Neurocomputing, 144 (2014) 13-23.

Griffin, et al. "Small Bowel MR Enterography: Problem Solving in Crohn's Disease." Insights Imaging, 3 (2012) 251-263.

Mowat, et al. "Guidelines for the Management of Inflammatory Bowel Disease in Adults." Gut, 60 (2011) 571-607.

* cited by examiner

RADIOMIC FEATURES ON DIAGNOSTIC MAGNETIC RESONANCE ENTEROGRAPHY

CROSS REFERENCE TO RELATED APPLICATIONS

This application claims the benefit of U.S. Provisional Application 62/272,762 filed Dec. 30, 2015.

FEDERAL FUNDING NOTICE

The invention was made with government support under grants DK098503, CA179327, CA195152, CA199374, awarded by the National Institutes of Health. Also, grants W81XWH-13-1-0418, W81XWH-14-1-0323, and W81XWH-16-1-0329 awarded by the Department of Defense. The government has certain rights in the invention.

BACKGROUND

Crohn's disease (CD) affects up to 700,000 people in the United States. CD primarily affects younger adult patients. CD is difficult to diagnose because CD often presents nonspecific symptoms that may be associated with numerous, different, pathologies. A large proportion of CD cases involve the small bowel, and may involve the full thickness of the bowel wall. Additionally, the structural complexity of the small bowel can make interpretation of symptoms difficult. Thus, conventional approaches such as biopsies are not optimal for predicting patient response to treatment since biopsies may only assess superficial tissues and not the full thickness of the bowel wall, and may not be able to access the small bowel.

CD management involves early prediction of patient response to immunosuppressive (IS) therapy. Therapy decisions for patients suffering from CD or CD related symptoms are often based on patient symptoms, and are therefore subjective. Thus, therapy decisions for many patients result in poor outcomes. For example, up to 40% of patients may not respond to initial IS therapy, and may instead suffer from increasingly severe small bowel inflammation. Further complicating the diagnosis and treatment of CD is the lack of effective biomarkers to predict patient outcomes.

Magnetic resonance enterography (MRE) is a safe, non-invasive means of imaging CD presence and activity in vivo. MRE does not use harmful radiation, and, since it is non-ionizing, can therefore be used to obtain imagery of younger patients or patients who may need to undergo a large number of future imaging procedures. However, the application of MRE to early prediction of patient response to IS therapy is limited by poor inter-rater agreement and is also consequently subjective. Furthermore, the effective application of MRE to early prediction of patient response to IS therapy is limited by the lack of a definitive disease scoring system for CD.

CD response to IS therapy is conventionally assessed using the Crohn's Disease Endoscopic Index of Severity (CDEIS). CDEIS is, however, indicative of severity and not treatment outcome, and is thus not optimal when used to predict patient response to IS therapy. Another tool for assessing CD in a patient is the Magnetic Resonance Index of Activity (MaRIA). MaRIA indicates the severity of CD, and may be correlated with CDEIS. However, MaRIA is based on an expert evaluation, and is thus largely subjective. Furthermore, a patient's treatment response or outcome may not correlate with the severity of CD determined by CDEIS or MaRIA. Thus, predictive scores based on CDEIS or MaRIA are highly variable.

Since radiologists may be challenged to reliably predict patients' response to IS therapy using conventional approaches in clinically relevant time frames, ineffective therapies and procedures may be performed that ultimately result in no improvements for the patient. Patients who are provided with ineffective therapies may be subjected to treatment escalation that could otherwise be avoided. Treatment escalation, including hospitalization, medication escalation, or invasive procedures such as surgery or stricturoplasty, takes time, costs money, wastes resources that could be more beneficially employed, and puts a patient at additional risk. Therefore, CD patients would benefit from an accurate, non-invasive predictor of IS therapy response that facilitated more accurate and effective treatment of CD.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
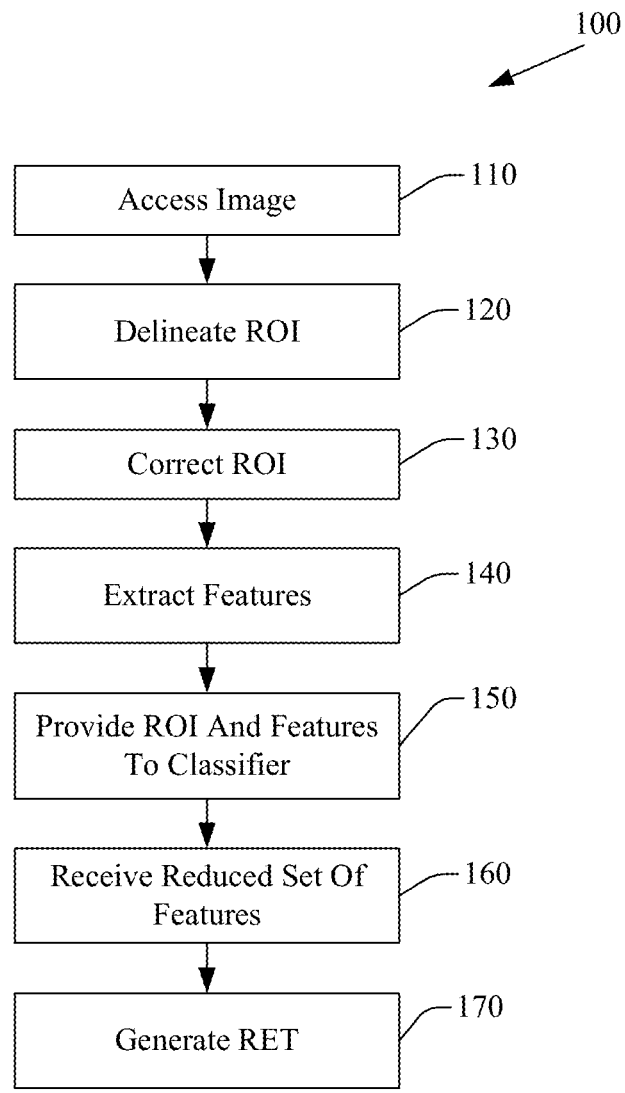
FIG. 1 illustrates an example method for predicting response to IS therapy in a region of tissue demonstrating CD pathology.

Example methods and apparatus quantitatively evaluate MRE imagery data of a region of tissue demonstrating CD using radiomics to discriminate between responders and non-responders to IS therapy. Example methods and apparatus extract quantitative features from radiographic images, including MRE images, to capture subtle differences of disease appearance. Example methods and apparatus quantify higher order information in radiographic images that is not discernible upon visual inspection by a human to facilitate improved discrimination of treatment response in patients demonstrating CD. Example methods and apparatus apply machine learning to radiomics data captured from baseline MRE imagery and use a reduced dimensionality radiomic enterographic treatment (RET) score to facilitate predicting patient response to IS treatment.

Variations in response to IS treatment of CD may be related to patient prognosis and outcome. Conventional methods of planning IS therapy to treat CD rely on subjective decisions made based on patient symptoms, or rely on analysis of biopsied tissue. However, invasive biopsies and surgical procedures may not always be a convenient or appropriate method for predicting responsiveness to IS therapy. Invasive biopsies and surgical resections cost money, take time, and put a patient at additional risk. A non-invasive approach that provided improved accuracy compared to conventional approaches would reduce unnecessary treatment escalation, reduce the number of unnecessary interventions, reduce the dependency on repetitive or higher resolution radiological exams, offer a non-invasive means of assessing response to targeted therapies, and improve patient outcomes. Thus, a timely, non-invasive procedure that results in more accurate prediction of response to IS therapy, would offer reduced risk to patients while providing economic benefits to the health care system.

Example methods and apparatus predict patient outcomes more accurately than conventional methods by employing computerized textural and morphological analysis of MRE imagery to predict the likelihood a ROI will respond to IS therapy. An ROI may be defined as an annotation of Crohn's extent with respect to healthy tissue represented on an MRE image. Example methods and apparatus may delineate the ROI from background tissue automatically, or the ROI may be delineated by an expert human radiologist. Features may be extracted from the ROI. The features extracted from the ROI may include first order statistical features, second order statistical features, oriented wavelets, including Gabor features, non-oriented wavelets such as Haar features or Laplace features, or local neighborhood-based texture energy features, including Laws features and local binary pattern features, and shape descriptors that quantify information including but not restricted to roundness, eccentricity, irregularity, and size of the ROI. In some embodiments, at least ninety-five features are extracted from the ROI. A subset of extracted features may be selected using principal component analysis (PCA), including PCA-variable importance projection (PCA-VIP) analysis. In one embodiment, the subset of extracted features may be selected using non-linear methods. Non-linear methods may include spectral embedding (SE), including Feature Importance in Non-linear Embedding (FINE) analysis. The subset of extracted features may include features that are more discriminative than other, non-selected features. A classification of the ROI may be generated using quadratic discriminant analysis (QDA) or linear discriminant analysis (LDA) of the subset of extracted features. Example methods and apparatus reduce the dimensionality of the subset of extracted features to generate a radiomic enterographic treatment (RET) score. The RET score may be a one-dimensional score that indicates the likelihood the ROI will respond to IS therapy. For example, in one embodiment, an ROI with an RET score of 0 may be more likely to respond to IS therapy than an ROI with an RET of 1. Other classifications or scales may be employed.

Example methods and apparatus may train and test a classifier. The classifier may be a linear discriminant analysis (LDA) classifier, a support vector machine (SVM) classifier, a random forest, or other type of machine-learning based classifier. In one embodiment, example methods and apparatus employ a set of training images of tissue demonstrating response to IS or non-response to IS, for training the classifier, and a set of testing images for testing the classifier. For example, a human radiologist may manually delineate and classify one hundred ROIs for a training set and thirty ROIs for a testing set using accepted MRE criteria, including MaRIA or CDEIS. Example methods and apparatus may then train the classifier using the training set and test the classifier using the testing set to classify the ROIs represented in the testing set as likely to respond to IS or unlikely to respond to IS. Other sizes or numbers of training sets or sizes or numbers of testing sets may be employed.

Example methods and apparatus thus improve on conventional methods by more accurately predicting patient response to IS therapy. Example methods and apparatus distinguish responders to IS therapy from non-responders to IS therapy with an accuracy of at least 0.77 AUC when using ten features extracted from an ROI with an LDA classifier. Example methods and apparatus predict one year unfavorable outcomes (e.g. surgery, resection, stricturoplasty, hospitalization, medication escalation) with an accuracy of 0.8 AUC. Example methods and apparatus predict end-of-follow-up unfavorable outcomes at a median time of one-hundred and twenty days with an accuracy of 0.99 AUC. Example methods and apparatus predict one-year surgical outcomes at a median time of one-hundred and nineteen days with an accuracy of 0.71 AUC. Example methods and apparatus predict end-of-follow-up surgical outcomes at a median time of one-hundred fifty nine days with an AUC of 0.74. In contrast, conventional approaches for predicting response to IS therapy are highly subjective, variable, and less accurate than example methods and apparatus. For instance, the MaRIA index suffers from a very variable inter-observer variability, demonstrating a poor intra-class correlation coefficient (ICC) of 0.23-0.79-0.14. Additionally, some conventional approaches that assess bowel thickening with contrast enhanced MRE analyzed together at week zero were associated with steroid-free remission at week fifty-two with an AUC of 0.67. Example methods and apparatus thus facilitate a significant, measurable increase in accuracy compared to conventional approaches.

By increasing the accuracy with which response to treatment is predicted, example methods and apparatus produce the concrete, real-world technical effect of reducing the time required to evaluate medical imagery while increasing the accuracy of the evaluation. Additionally, example apparatus and methods increase the probability that at-risk patients receive timely treatment tailored to the particular pathology they exhibit. Example methods and apparatus may also reduce the number of invasive procedures needed to accurately characterize or plan treatment for CD. The additional technical effect of reducing the expenditure of resources and time on patients who are less likely to suffer recurrence or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, circuit, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates an example computerized method 100 for predicting response to IS treatment. Method 100 includes, at 110, accessing a radiological image of a region of tissue demonstrating Crohn's Disease (CD) pathology. Accessing the radiological image may include accessing a gadolinium contrast magnetic resonance enterography (MRE) image of the region of tissue. Accessing the image may also include accessing another type of medical image of a region of tissue demonstrating a different, non-CD pathology. Accessing the image may include retrieving electronic data from a computer memory, receiving a computer file over a computer network, or other computer or electronic based action. In one embodiment, the image is acquired using a true fast imaging sequence with steady precession and fat suppression (TRUFIFS). In another embodiment, a volumetric interpolated breath-hold examination (VIBE) sequence, or a half-Fourier acquisition single-shot turbo spin-echo (HASTE) sequence may be employed to acquire the image. In another embodiment, other sequences or combinations of sequences may be employed.

Method 100 also includes, at 120, delineating a region of interest (ROI) in the image. The ROI may be delineated by an expert radiologist. The ROI may be delineated based, at least in part, on a magnetic resonance index of activity (MaRIA) criterion. The MaRIA criterion may be correlated with a Crohn's disease endoscopic index of severity (CDEIS) measurement of the ROI. In one embodiment, the ROI is delineated automatically.

Method 100 also includes, at 130, generating a corrected ROI. Method 100 generates the corrected ROI by bias field corrected the ROI. Bias field correcting the ROI reduces intensity variation across the image. Bias field correction may also reduce image intensity variation across patients, or between images acquired from different institutions. In one embodiment, bias field correcting the ROI includes removing acquisition-related intensity variations across the ROI during a preprocessing step using a surface fitting approach. Bias field correcting the ROI may include applying low-pass filtering to correct inhomogeneity in the ROI.

Method 100 also includes, at 140, extracting a set of features from the corrected ROI. The set of features includes at least ninety-five voxel-wise or pixel-wise features extracted from the corrected ROI. The at least ninety-five features includes a first order statistical feature, a second order statistical feature, an intensity feature, a Laws texture feature, a local binary pattern (LBP), a Haralick feature, a gradient orientation feature, including a co-occurrence of local anisotropic gradient orientations (CoLIAGe) feature, or a Gabor feature. The first order or second order statistical features may capture intensity characteristics of the corrected ROI, including heterogeneity or homogeneity. Laws texture features or LBPs capture the arrangement of intensities in the ROI, expressing structures including spots, ripples, or waves. Gradient-based features, including gradient orientations or CoLIAGe features capture the directionality or multi-scale response of inflamed bowel wall tissue and lumen represented in the ROI. CoLIAGe features capture differences between tissue that is likely to respond to IS compared to tissue that is less likely to respond to IS, which, even though they may have very similar overall texture and appearance on imaging, at a local scale, will have different co-occurring patterns with respect to gradient orientations. In another embodiment, other numbers of voxel-wise or pixel-wise features may be extracted. In another embodiment, other features may be extracted, at other, different resolutions.

In one embodiment, the set of features extracted from the corrected ROI includes a Laws spot-wave standard deviation feature, a CoLIAGe sum entropy-kurtosis feature, a Laws wave-wave skewness feature, a Laws wave-wave standard deviation feature, and a Gabor standard deviation feature. In one embodiment, the set of features extracted includes, a CoLIAGe difference-variance skewness feature, a Laws edge-ripple standard deviation feature, a Haralick inverse difference moment skewness feature, a Laws level-ripple mean feature, and a CoLIAGe difference entropy kurtosis feature. CoLIAGe features include statistics of dominant gradient orientation co-occurrence matrices. Haralick calculations computed on first derivative gradient orientations may be extracted from the CoLIAGe features. The set of features may also include non-oriented wavelets such as Haar features or Laplace features. The set of features may also include local neighborhood-based texture energy features, local binary pattern features, and shape descriptors that quantify information including but not restricted to roundness, eccentricity, irregularity, and size of the ROI. In some embodiments, at least ninety-five features are extracted from the ROI. Other features may also be extracted, and other statistics may be calculated.

Method 100 also includes, at 150, providing the corrected ROI and the set of features to an automated CD classifier. Providing the corrected ROI and the set of features to the automated CD classifier may include retrieving electronic data from a computer memory, transmitting or receiving a computer file over a computer network, or other computer or electronic based action.

Method 100 also includes, at 160, receiving a reduced set of features from the automated CD classifier. The automated CD classifier may be a linear discriminant analysis classifier that generates the reduced set of features. In another embodiment, other, different types of machine-learning classifiers may be employed, including support vector machines or random forests. The reduced set of features is based, at least in part, on the corrected ROI or the set of features. The reduced set of features may be a weighted set of features. In one embodiment, the automated CD classifier generates the reduced set of features using a Wilcoxon rank sum test with 5-fold cross-validation and 100 runs. The Wilcoxon rank sum test may select the top four most discriminative features during a run. A discriminative feature is a feature that demonstrates separation between different classes (e.g. responder to IS, non-responder to IS). Example methods and apparatus described herein may quantify a level of discriminability of a feature using a Bhattacharyya distance. In one embodiment, the reduced set of features includes at least ten features. The at least ten features includes a gradient orientation feature based on a difference entropy of directionality, or a multi-scale oriented Gabor feature. A member of the reduced set of features may capture a combined response for both inflamed bowel wall regions and lumen regions within the ROI, capturing both disease activity and severity. In another embodiment, different approaches may be employed to select the reduced set of features.

Method 100 further includes, at 170, controlling a computer aided diagnosis (CADx) system to generate a radiomic enterographic treatment (RET) score of the region of tissue. The RET score is based, at least in part, on the reduced set of features. The RET score represents a probability that the region of tissue will respond to IS therapy. The RET score is a one-dimensional (1D) projection of the reduced set of features. The RET score may be computed using a principal component analysis (PCA) or SE of the reduced set of features. In one embodiment, example methods and apparatus project radiomics features, including median, variance, skewness, or kurtosis, over the pixels or voxels within an ROI into a three-dimensional (3D) Eigen space. Example methods and apparatus may display the RET or the 3D Eigen space projection on a computer monitor, on a tablet computer, on a smart phone display, or on another display device. By providing a quantifiable, visual representation of the likelihood a region of tissue will respond to IS, example methods and apparatus facilitate the optimization of patient therapy management for CD, and facilitate the reduction of the number or frequency of invasive procedures to assess treatment response, thereby improving patient outcomes, and reducing costs associated with CD treatment.

In one embodiment, method 100 also controls the CADx system to generate a classification of the ROI. The classification of the ROI may be based, at least in part, on the reduced set of features, the RET score, or the probability that the ROI will respond to IS therapy. Method 100 may classify the ROI as a responder, or as a non-responder. The classification of the ROI facilitates the timely, efficient, and accurate application of IS therapy, or other treatment modalities.

In one embodiment, the reduced set of features is selected by reducing the set of features using a PCA-VIP approach or a FINE approach. In another embodiment, first order statistics may be derived from different radiomic descriptor families (e.g. Haralick, Laws Energy, histogram of oriented gradients (HoG), or Gabor). The reduced set of features may be selected after running one-hundred iterations of five-fold cross validation using an Area Under the receiver-operating characteristic Curve (AUC) using an LDA classifier. The most discriminative features may then be identified using a Feed Forward Feature Selection (FFFS) approach or a Maximum Relevance Minimum Redundancy approach. In one embodiment, the reduced set of features includes a kurtosis of a Haralick feature, a mean of the Haralick feature, a kurtosis of a Laplacian, and a mean of a Law feature. In another embodiment, the reduced set of features includes a mean of a Gabor feature, a standard deviation of the Gabor feature, a mean of the Gabor feature, and a median of an HoG.

In another embodiment, example methods and apparatus employ a PCA or SE of the set of features to select the reduced set features from the set of features. The reduced set of features may achieve a threshold level of discriminability. For example, the PCA or SE may select one energy feature and one Gabor feature that are the most discriminative, based on a particular set of MRE images, for distinguishing IS responders from IS non-responders. The level of discriminability may be user adjustable. For example, in a first clinical situation, a reduced set features that achieves 0.70 AUC accuracy in distinguishing response to IS therapy from non-response to IS therapy may be acceptable. In another embodiment, a 0.77 AUC may be acceptable. A feature may be considered to have a desirable level of discriminability when the means of two separate classes are more than a threshold distance from each other, and where the variance of a class is less than a threshold distance, in comparison to the distance between the means. In one embodiment, the Bhattacharyya distance may be used to quantitatively establish a desirable level of discriminability.

Figure 6:
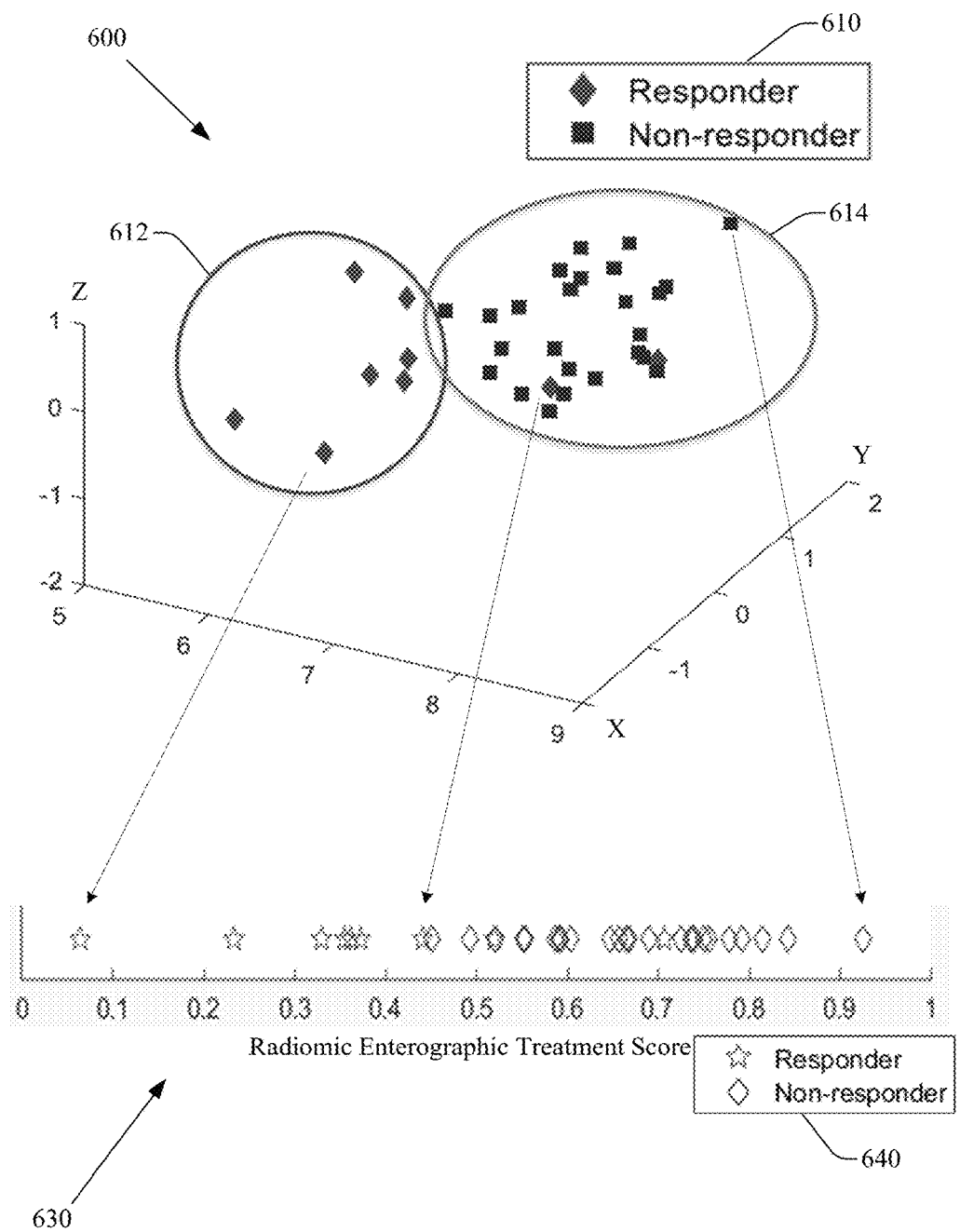
FIG. 6 illustrates a three-dimensional scatter plot and a one-dimensional radiomic enterographic treatment (RET) score graph of responders and non-responders to IS therapy.

FIG. 6 illustrates a scatter plot 600 of a cohort of CD patients who responded to or did not respond to IS therapy. Scatter-plot legend 610 indicates symbols used to represent responders or non-responders. Scatter plot 600 illustrates responders in a first cluster 612 and non-responders in a second cluster 614. Scatter plot 600 plots the responders and non-responders on three axes, which correspond to different discriminative features extracted from an ROI. In this example, the X axis represents a first feature, the Y axis represents a second feature, while the Z axis represents a third feature. The first feature may be, for example, a CoLIAGe feature, the second feature may be, for example, a first macro-scale Gabor feature, while the third feature may be, for example, a second macro-scale Gabor feature. Recall that example methods and apparatus are not limited to three features, but may employ a reduced set of features that includes ten features, or other numbers of features. The responders and non-responders illustrated in three dimensions by scatter plot 600 are reduced to a one-dimensional RET score 630. In the example illustrated in FIG. 6, example methods and apparatus employ PCA to reduce the dimensionality of the features represented in three-axis scatter plot 600 to the one dimensional RET score 630. RET scale legend 640 indicates symbols used to represent responders or non-responders by RET score 630.

While FIG. 1 illustrates various actions occurring in serial, it is to be appreciated that various actions illustrated in FIG. 1 could occur substantially in parallel. By way of illustration, a first process could access an MRE image, a second process could delineate a region of interest in the image, and a third process could extract radiomic features from the MRE image. While three processes are described, it is to be appreciated that a greater or lesser number of processes could be employed and that lightweight processes, regular processes, threads, and other approaches could be employed.

Figure 2:
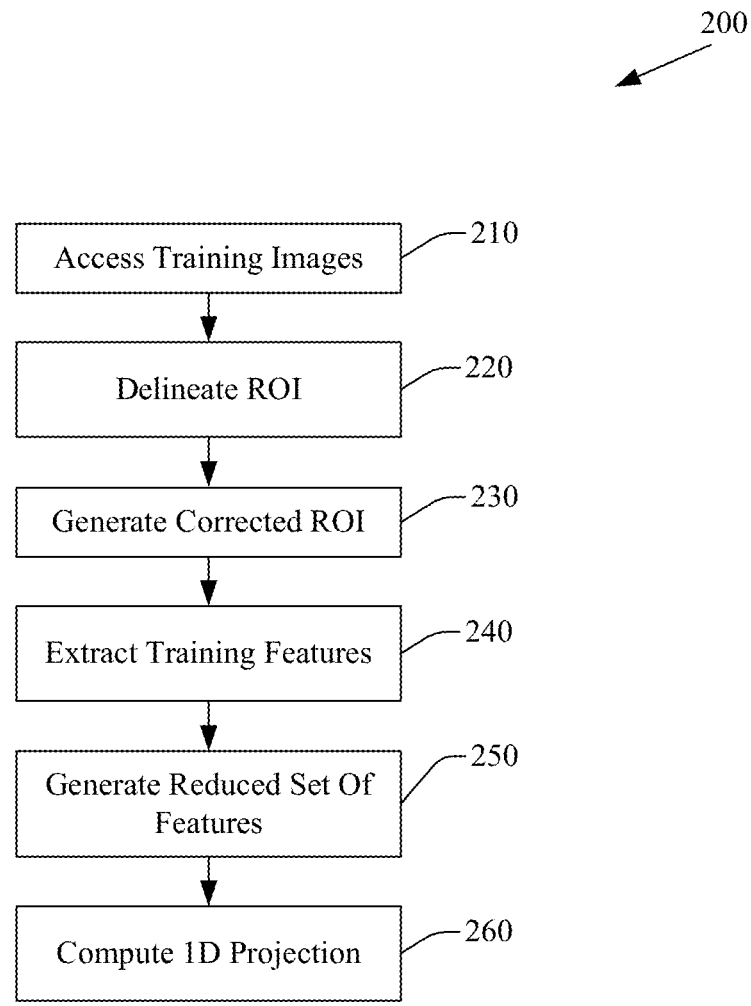
FIG. 2 illustrates an example method of training an automated CD classifier.

FIG. 2 illustrates an example method 200 for training an automated CD classifier. Method 200 includes, at 210, accessing a set of training images. The set of training images includes an image of a region of tissue demonstrating CD pathology. The set of training images includes an image of a region of tissue demonstrating CD pathology that responded to IS therapy. The set of training images also includes an image of a region of tissue demonstrating CD pathology that did not respond to IS therapy. Accessing the set of training images may include retrieving electronic data from a computer memory, receiving a computer file over a computer network, or other computer or electronic based action. In one embodiment, the set of training images is acquired using a true fast imaging sequence with steady precession and fat suppression (TRUFIFS). In another embodiment, other sequences may be employed. The set of training images may be acquired from a single institution, including a hospital or university, or may be acquired from a plurality of institutions.

Method 200 also includes, at 220, delineating an ROI in a member of the set of training images. In one embodiment, the ROI is delineated by an expert human radiologist. The ROI may be delineated based on a MaRIA criterion. In another embodiment, the ROI is delineated automatically by a computerized segmentation system.

Method 200 also includes, at 230, generating a corrected ROI associated with the member of the set of training images. Generating a corrected ROI includes bias field correcting the ROI. Bias field correcting the ROI includes reducing intensity variations across an image. Bias field correcting the ROI may also include reducing intensity variations across images acquire from different patients from which a first member of the set of training images and a second member of the set of training images are acquired.

Method 200 also includes, at 240, extracting a set of training features from the corrected ROI. In one embodiment, the set of training features includes at least ninety-five features. The at least ninety-five features may be pixel-wise or voxel-wise features. The at least ninety-five features includes a first order statistical feature, a second order statistical feature, an intensity feature, a Laws texture feature, a local binary pattern (LBP), a Haralick feature, a gradient orientation including a co-occurrence of local anisotropic gradient orientations (CoLIAGe) feature, or a Gabor feature. The at least ninety-five features may include a Laws spot-wave standard deviation feature, a CoLIAGe sum entropy-kurtosis feature, a Laws wave-wave skewness feature, a Laws wave-wave standard deviation feature, or a Gabor standard deviation feature. The at least ninety five features may further include non-oriented wavelets such as Haar features or Laplace features. The at least ninety five features may also include local neighborhood-based texture energy features, and shape descriptors that quantify information including but not restricted to roundness, eccentricity, irregularity, and size of the corrected ROI. In another embodiment, other numbers or types of training features may be extracted from the corrected ROI.

Method 200 also includes, at 250, generating a reduced set of features based, at least in part, on the set of training features. Method 200 selects a first threshold number of features from the set of training features. In one embodiment, the first threshold number of features is ten. The first threshold number of features are selected using a Wilcoxon rank sum test based on a five-fold cross validation of a second threshold number of runs. In one embodiment, the second threshold number of runs is one-hundred. In another embodiment, the first threshold number of features or the second threshold number of runs may be other, different numbers. The Wilcoxon rank sum test selects at least one of the first threshold number of features that discriminates between an image of a region of tissue demonstrating CD pathology that responded to IS therapy, and an image of a region of tissue demonstrating CD pathology that did not respond to IS therapy. The Wilcoxon rank sum test may base the selection of the feature, at least in part, on a Bhattacharyya distance. In another embodiment, the first threshold number of features are selected using a different selection technique.

Method 200 further includes, at 260, computing a 1D projection of the reduced set of features. The 1D projection may be computed using a PCA or SE analysis of the reduced set of features. In another embodiment, the 1D projection may be computed using other, different dimensionality reducing approaches.

Figure 3:
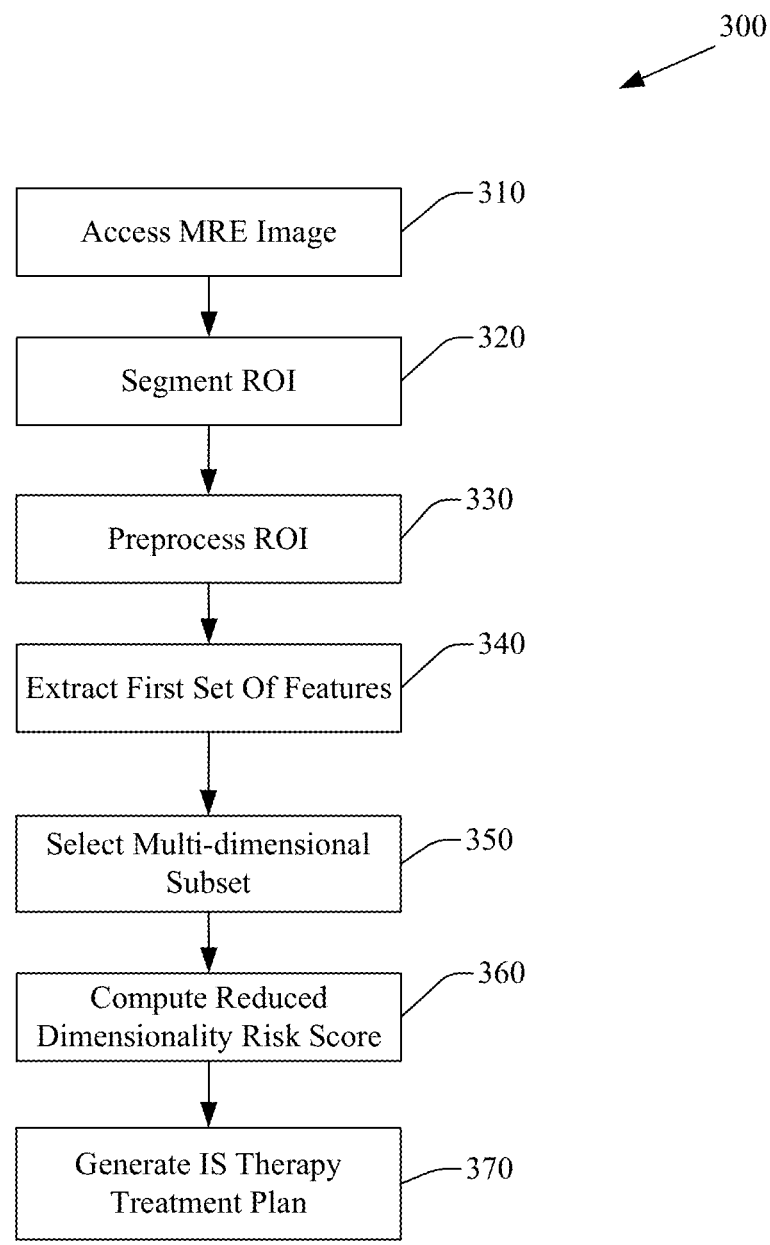
FIG. 3 illustrates an example method for planning IS therapy.

FIG. 3 illustrates an example method 300 for planning IS therapy for a patient demonstrating CD pathology. Method 300 includes, at 310, accessing an MRE image of a region of tissue demonstrating CD pathology. Accessing the MRE image may include accessing a gadolinium contrast MRE image of the region of tissue. Accessing the MRE image may also include accessing another type of medical image of a region of tissue demonstrating a different, non-CD pathology. Accessing the MRE image may include retrieving electronic data from a computer memory, receiving a computer file over a computer network, or other computer or electronic based action. In one embodiment, the image is acquired using a true fast imaging sequence with steady precession and fat suppression (TRUFIFS).

Method 300 also includes, at 320, segmenting a region of interest (ROI) in the image from the background of the MRE image. The ROI may be segmented by an expert human radiologist, or may be segmented automatically by a computerized segmentation system. The segmentation may be based on a MaRIA criterion, or may be based on other CD segmentation guidelines.

Method 300 also includes, at 330, generating a preprocessed ROI by removing intensity variations from the ROI. Preprocessing the ROI may include bias field correction of the ROI to reduce intensity variations across the ROI, across multiple ROIs acquired from multiple MRE images, or across MREs acquired from multiple institutions or multiple patients.

Method 300 also includes, at 340, extracting a first set of features from the preprocessed ROI. The first set of features may include a first order statistical feature, a second order statistical feature, an intensity feature, a Laws feature, a local binary pattern feature, a gradient orientation feature, or a Gabor feature. In one embodiment, the first set of features includes at least ninety-five features.

Method 300 also includes, at 350, selecting a multi-dimensional subset of discriminative features from the first set of features. The multi-dimensional subset of discriminative features includes a gradient orientation feature. In one embodiment, the multi-dimensional subset of discriminative features includes at least ten features. The at least ten features includes a gradient orientation feature. The gradient orientation feature is based on gradient orientations of the ROI, where a magnitude of chaos or a magnitude of change in directionality corresponds to a level of non-response to IS therapy.

Method 300 also includes, at 360, computing a reduced-dimensionality personalized risk score based, at least in part, on the multi-dimensional subset of discriminative features. Method 300 computes the reduced-dimensionality personalized risk score using a PCA or SE of the multi-dimensional subset of discriminative features. The reduced-dimensionality personalized risk score represents the probability that the ROI will respond to IS therapy. In one embodiment, the reduced-dimensionality personalized risk score is a 1D RET score.

Method 300 further includes, at 370, generating an IS therapy treatment plan. The IS therapy treatment plan is based, at least in part, on the reduced-dimensionality personalized risk score. In one embodiment, the IS therapy treatment plan is generated based on the 1D RET score. The IS therapy treatment plan may be further based on the ROI or the MRE image.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, or method 300. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 4:
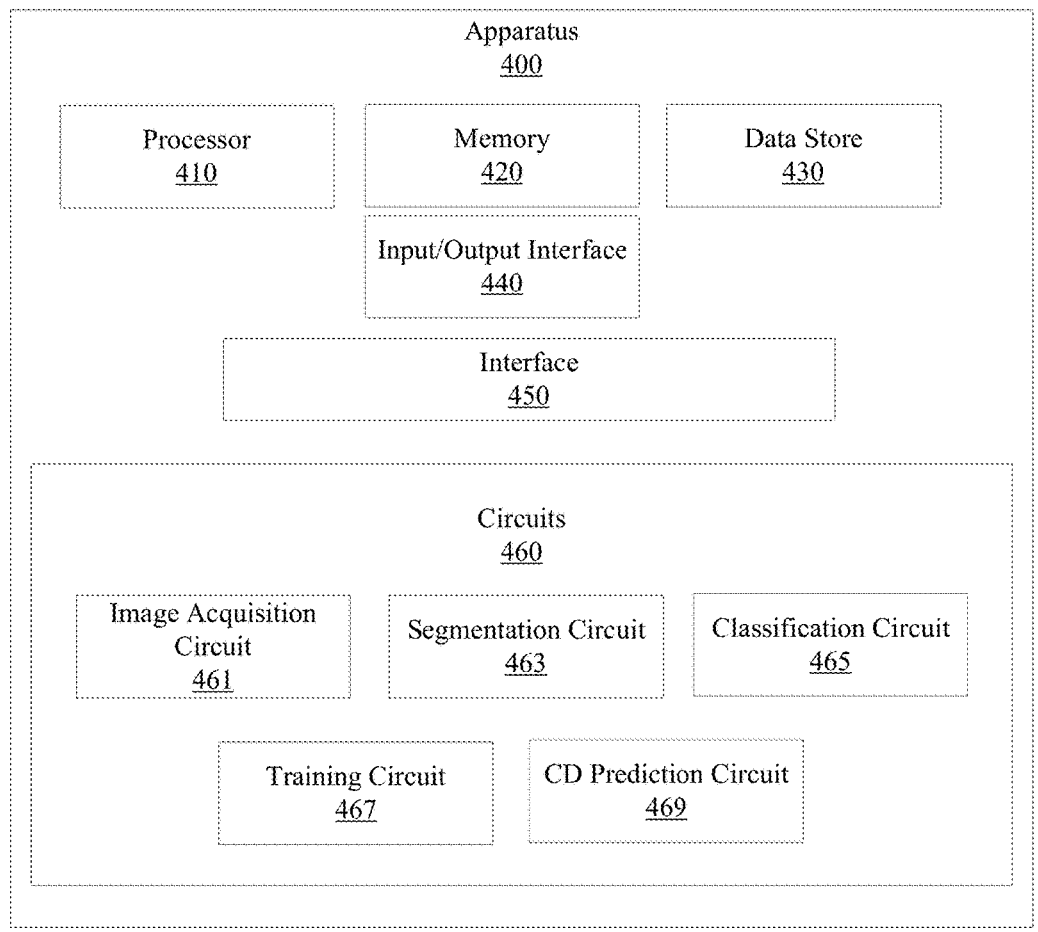
FIG. 4 illustrates an example apparatus that classifies a region of tissue in an MRE image.

FIG. 4 illustrates an example apparatus 400 for classifying a region of tissue in an image. Apparatus 400 includes a processor 410, a memory 420, a data store 430, an input/output (I/O) interface 440, a set of circuits 460, and an interface 450 that connects the processor 410, the memory 420, the data store 430, the I/O interface 440, and the set of circuits 460. The set of circuits 460 includes an image acquisition circuit 461, a segmentation circuit 463, a classification circuit 465, a training circuit 467, and a CD prediction circuit 469. In one embodiment, the functionality associated with the set of circuits 460 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 460 are implemented as ASICs or SOCs.

Data store 430 stores a set of training radiological images of a region of tissue demonstrating Crohn's Disease. The set of training radiological images may include an image of a region of tissue that has been determined to be non-responsive to IS therapy. A member of the set of training radiological images may be a gadolinium contrast MRE image acquired using a TRUFIFS sequence. The set of training radiological images also includes an image of a region of tissue that has been determined to be responsive to IS therapy. A member of the set of training radiological images includes a first set of features. The first set of features includes a first order statistical feature, a second order statistical feature, an intensity feature, a Laws feature, a local binary pattern feature, a gradient orientation feature, or a Gabor feature. The first set of features may also include non-oriented wavelets such as Haar features or Laplace features. In another embodiment, the first set of features may include other, different features. Data store 430 may also store a set of testing images of a region of tissue demonstrating CD pathology. A member of the set of testing images may include a set of features similar to the first set of features. A member of the set of testing images or the set of testing images may be a gadolinium contrast MRE image acquired using a TRUFIFS sequence.

Image acquisition circuit 461 accesses a diagnostic radiological image of a region of tissue demonstrating CD pathology in a patient. The diagnostic radiological image may be acquired from, for example, an MRE apparatus. In one embodiment, accessing the image may include accessing a gadolinium contrast MRE image of the region of tissue. Accessing the image may also include accessing another type of medical image of a region of tissue demonstrating a different, non-CD pathology. Accessing the image may include retrieving electronic data from a computer memory, receiving a computer file over a computer network, or other computer or electronic based action. In one embodiment, the image is acquired using a TRUFIFS sequence. In another embodiment, other sequences, including a HASTE sequence or a VIBE sequence may be employed. In another embodiment the image could be a subtraction or delayed acquisition derived from one of the above sequences. Image acquisition circuit 461 provides the diagnostic radiological image to segmentation circuit 463. In another embodiment, other sequences may be employed. Other imaging approaches may be used to generate and access the image accessed by image acquisition circuit 461.

Segmentation circuit 463 segments or delineates an ROI by distinguishing CD tissue within the diagnostic radiological image from the background of the diagnostic radiological image. Segmentation circuit 463 bias field corrects the segmented ROI. Bias field correcting the ROI includes reducing intensity variation across the diagnostic radiological image, or reducing intensity variation between diagnostic radiological images acquired from different patients, or between diagnostic radiological images acquired from different institutions, or between diagnostic radiological images acquired using different MRE imaging parameters. In one embodiment, segmentation circuit 463 automatically delineates the ROI using threshold based segmentation, deformable boundary models, active-appearance models, active shape models, graph based models including Markov random fields (MRF), min-max cut approaches, or other image delineation approaches. In one embodiment, segmentation circuit 463 is configured to facilitate a human radiologist delineating the ROI. Segmentation circuit 463 may define a ROI boundary. The ROI comprises a second set of features. The second set of features includes a first order statistical feature, a second order statistical feature, an intensity feature, a Laws feature, a local binary pattern feature, a gradient orientation feature, or a Gabor feature. The second set of features may also include non-oriented wavelets such as Haar features or Laplace features. Segmentation circuit 463 provides the ROI to classification circuit 465.

Classification circuit 465 extracts a set of discriminative features from the ROI. The set of discriminative features distinguishes the ROI represented in the diagnostic radiological image as a responder to IS therapy, or as a non-responder to IS therapy. In one embodiment, classification circuit 465 extracts the set of discriminative features from the diagnostic radiological image using a Wilcoxon rank sum test. The Wilcoxon rank sum test may be based on a five-fold cross-validation with 100 runs. In another embodiment, the Wilcoxon rank sum test may be based on a three-fold or other integer number fold cross validation, with another, different number of runs. The set of discriminative features includes a Gabor feature, or a gradient orientation feature based on a difference entropy of directionality. The set of discriminative features may also include non-oriented wavelets such as Haar features or Laplace features. The set of discriminative features may be ranked according to a level of discriminability based, at least in part, on a Bhattacharyya distance.

Training circuit 467 trains classification circuit 465 to identify a first member of the first set of features associated with response to IS therapy, or to identify a second member of the first set of features associated with non-response to IS therapy, using the set of training radiological images or the set of testing images.

CD prediction circuit 469 generates an RET score based, at least in part, on the diagnostic radiological image or the set of discriminative features. In one embodiment, CD prediction circuit 469 generates the RET score by reducing the dimensionality of the set of discriminative features using PCA or SE. In another embodiment, CD prediction circuit 469 reduces the dimensionality of the set of discriminative features using a PCA-VIP approach, or other dimensionality reducing technique.

In one embodiment, the first set of features or the second set of features includes at least ninety-five voxel-wise features. The at least ninety-five voxel-wise features include a first order statistical feature, a second order statistical feature, an intensity feature, a Laws texture feature, a local binary pattern, a gradient orientation feature, or a Gabor feature. In another embodiment, the first set of features or the second set of features may include other numbers or types of features, including texture features or shape features, including a gray-level statistical feature, a steerable Gabor feature, a Haralick feature, a Law feature, a Law-Laplacian feature, an LBP feature, an inertia feature, a correlation feature, a difference entropy feature, a contrast inverse moment feature, a CoLlAGe feature, or a contrast variance feature. The first set of features or the second set of features may also include non-oriented wavelets including Haar features or Laplace features.

In another embodiment, CD prediction circuit 469 may control a CADx system to classify the diagnostic radiological image based, at least in part, on the RET score. For example, CD prediction circuit 469 may control a CD CADx system to classify the diagnostic radiological image based, at least in part, on the RET score, on the ROI, or on the set of discriminative features. In other embodiments, other types of CADx systems may be controlled, including CADx systems for distinguishing among breast cancer, oral cancer, prostate cancer, colon cancer, brain cancer, lung cancer, rectal cancer, and other diseases where disease classification and response to treatment prediction may be based on textural or shape features quantified from MRE images of a region of tissue demonstrating pathology that may be treatable with IS therapy.

In one embodiment of apparatus 400, the set of circuits 460 also includes a display circuit. The display circuit may control the CADx system to display the RET score, the first set of features or the second set of features, the set of discriminative features, the diagnostic radiological image, or the ROI, on a computer monitor, a smart phone display, a tablet display, or other displays. Displaying the RET score or the features may also include printing the classification or the features. The display circuit may also control the CADx to display an image of the ROI demonstrating CD pathology. The image of the ROI demonstrating CD pathology may include a delineated or segmented representation of the ROI. By displaying the RET score, the features, and the image of the ROI, example apparatus provide a timely and intuitive way for a human pathologist to more accurately classify pathologies demonstrated by a patient, thus improving on conventional approaches to predicting response to IS therapy.

Figure 5:
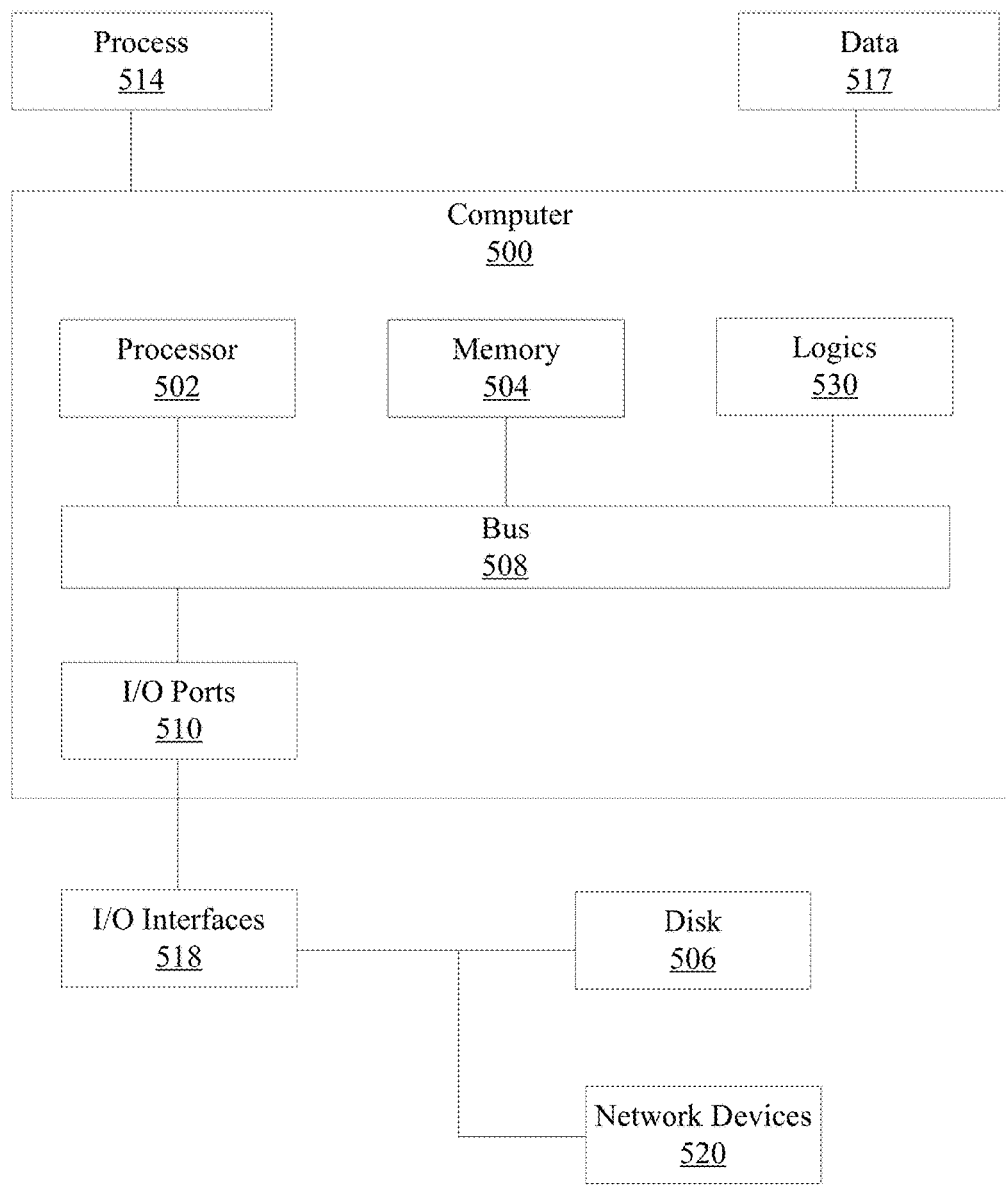
FIG. 5 illustrates an example computer in which example methods and apparatus may operate.

FIG. 5 illustrates an example computer 500 in which example methods illustrated herein can operate and in which example circuits or logics may be implemented. In different examples, computer 500 may be part of an MRE system or MRI system, may be operably connectable to an MRE system or MRI system, or may be part of a CADx system.

Computer 500 includes a processor 502, a memory 504, and input/output (I/O) ports 510 operably connected by a bus 508. In one example, computer 500 may include a set of logics 530 that perform a method of predicting response to IS therapy in a region of tissue demonstrating CD pathology, or a method for planning delivery of IS therapy. Thus, the set of logics 530, whether implemented in computer 500 as hardware or firmware, and/or a combination thereof may provide means (e.g., hardware, firmware) for predicting response to IS therapy in a region of tissue demonstrating CD pathology. In different examples, the set of logics 530 may be permanently and/or removably attached to computer 500. In one embodiment, the functionality associated with the set of logics 530 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 530 are implemented as ASICs or SOCs.

Processor 502 can be a variety of various processors including dual microprocessor and other multi-processor architectures. Memory 504 can include volatile memory and/or non-volatile memory. A disk 506 may be operably connected to computer 500 via, for example, an input/output interface (e.g., card, device) 518 and an input/output port 510. Disk 506 may include, but is not limited to, devices like a magnetic disk drive, a tape drive, a Zip drive, a solid state device (SSD), a flash memory card, a shingled magnetic recording (SMR) drive, or a memory stick. Furthermore, disk 506 may include optical drives like a CD-ROM or a digital video ROM drive (DVD ROM). Memory 504 can store processes 514 or data 517, for example. Disk 506 or memory 504 can store an operating system that controls and allocates resources of computer 500. Data 517 may include, for example, electronic files of MRE images of a region of tissue demonstrating CD.

Bus 508 can be a single internal bus interconnect architecture or other bus or mesh architectures. While a single bus is illustrated, it is to be appreciated that computer 500 may communicate with various devices, logics, and peripherals using other busses that are not illustrated (e.g., PCIE, SATA, Infiniband, 1394, USB, Ethernet).

Computer 500 may interact with input/output devices via I/O interfaces 518 and input/output ports 510. Input/output devices can include, but are not limited to, digital whole slide scanners, an MRE machine, and MRI system, an optical microscope, a keyboard, a microphone, a pointing and selection device, cameras, video cards, displays, disk 506, network devices 520, or other devices. Input/output ports 510 can include but are not limited to, serial ports, parallel ports, or USB ports.

Computer 500 may operate in a network environment and thus may be connected to network devices 520 via I/O interfaces 518 or I/O ports 510. Through the network devices 520, computer 500 may interact with a network. Through the network, computer 500 may be logically connected to remote computers. The networks with which computer 500 may interact include, but are not limited to, a local area network (LAN), a wide area network (WAN), or other networks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a non-transitory computer-readable medium that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, a data storage device, and other media from which a computer, a processor or other electronic device can read.

"Circuit", as used herein, includes but is not limited to hardware, firmware, software in execution on a machine, or combinations of each to perform a function(s) or an action(s), or to cause a function or action from another circuit, method, or system. Circuit may include a software controlled microprocessor, a discrete logic (e.g., ASIC), an analog circuit, a digital circuit, a programmed logic device, a memory device containing instructions, and other physical devices. Circuit may include one or more gates, combinations of gates, or other circuit components. Where multiple logical circuits are described, it may be possible to incorporate the multiple logics into one physical logic or circuit. Similarly, where a single logical circuit is described, it may be possible to distribute that single logic between multiple logics or circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer executable instructions that when executed by a computer, control the computer to perform a method for predicting a response to immunosuppressive (IS) therapy in a region of tissue, the method comprising:
    accessing a radiological image of a region of tissue demonstrating Crohn's Disease (CD) pathology;
    delineating a region of interest (ROI) in the image;
    generating a corrected ROI by bias field correcting the ROI;
    extracting a set of features from the corrected ROI;
    providing the corrected ROI and the set of features to an automated CD classifier;
    receiving, from the automated CD classifier, a reduced set of features based, at least in part, on the corrected ROI and on the set of features; and
    controlling a computer aided diagnosis (CADx) system to generate a radiomic enterographic treatment (RET) score of the region of tissue based, at least in part, on the reduced set of features, where the RET score represents a probability that the region of tissue responds to IS therapy.

2. The non-transitory computer-readable storage device of claim 1, where accessing the radiological image of the region of tissue comprises accessing a gadolinium contrast magnetic resonance enterography (MRE) image of the region of tissue.

3. The non-transitory computer-readable storage device of claim 2, where the MRE image is acquired using a true fast imaging sequence with steady precession and fat suppression (TRUFIFS), a volumetric interpolated breath-hold examination (VIBE) sequence, or a half-Fourier acquisition single-shot turbo spin-echo (HASTE) sequence.

4. The non-transitory computer-readable storage device of claim 1, where the set of features comprises at least ninety-five pixel-wise features extracted from the corrected ROI.

5. The non-transitory computer-readable storage device of claim 4, where the at least ninety-five pixel wise features include a first order statistical feature, a second order statistical feature, an intensity feature, a Laws texture feature, a local binary pattern, a gradient orientation feature, a Gabor feature, a Haar wavelet, or a Laplace feature.

6. The non-transitory computer-readable storage device of claim 5, where the automated CD classifier generates the reduced set of features using a Wilcoxon rank sum test with 5-fold cross-validation and 100 runs.

7. The non-transitory computer-readable storage device of claim 6, where the RET score is a one dimensional (1D) projection of the reduced set of features.

8. The non-transitory computer-readable storage device of claim 7, where the RET score is computed using a principal component analysis (PCA) of the reduced set of features or spectral embedding (SE) of the reduced set of features.

9. The non-transitory computer-readable storage device of claim 8, where the reduced set of features includes at least ten features, where the at least ten features includes a gradient orientation feature based on a difference entropy of directionality.

10. The non-transitory computer-readable storage device of claim 1, the method further comprising training the automated CD classifier, where training the automated CD classifier comprises:
    accessing a set of training images of tissue demonstrating CD pathology, where the set of training images includes an image of a region of tissue demonstrating CD pathology that responded to IS therapy, and an image of a region of tissue demonstrating CD pathology that did not respond to IS therapy;

delineating a training ROI in a member of the set of training images;

generating a corrected ROI by bias field correcting the training ROI;

extracting a set of training features from the corrected ROI;

generating a reduced set of features by selecting a first threshold number of features from the set of training features, where the first threshold number of features are selected using a Wilcoxon rank sum test based on a five-fold cross validation of a second threshold number of runs, where the Wilcoxon rank sum test selects a feature that discriminates between an image of a region of tissue demonstrating CD pathology that responded to IS therapy, and an image of a region of tissue demonstrating CD pathology that did not respond to IS therapy based, at least in part, on a Bhattacharyya distance; and computing a 1D projection of the reduced set of features using a principal component analysis (PCA) or spectral embedding (SE) of the reduced set of features.

11. The non-transitory computer-readable storage device of claim 10, where the first threshold number of features is ten, and where the second threshold number of runs is 100.

12. The non-transitory computer-readable storage device of claim 1, where bias field correcting the ROI comprises removing acquisition-related intensity variation across the ROI.

13. The non-transitory computer-readable storage device of claim 1, where delineating the ROI comprises annotating the image based on a magnetic resonance index of activity (MaRIA) criterion.

14. The non-transitory computer-readable storage device of claim 1, where the CADx system generates the RET score using a linear discriminant analysis (LDA) classifier, where the RET score represents the probability that the region of tissue will respond to IS therapy with an accuracy of at least 0.77 area under the curve (AUC).

15. An apparatus, comprising:
a processor;
a memory;
a data store that stores a set of training radiological images of tissue demonstrating Crohn's Disease (CD), where a member of the set of training radiological images represents a region of tissue that is non-responsive to immunosuppressive (IS) therapy or a region of tissue that is responsive to IS therapy, where the member of the set of training radiological images includes a first set of features;
an input/output interface;
a set of circuits, where the set of circuits includes an image acquisition circuit, a segmentation circuit, a classification circuit, a training circuit, and a CD prediction circuit; and
an interface to connect the processor, the memory, the data store, the input/output interface and the set of circuits:
where the image acquisition circuit accesses a diagnostic radiological image of a region of tissue demonstrating CD pathology, where the image acquisition circuit provides the diagnostic radiological image to the segmentation circuit;

where the segmentation circuit segments a region of interest (ROI) from the diagnostic radiological image, where the segmentation bias field corrects the ROI, where the segmentation circuit provides the ROI to the classification circuit, where the ROI includes a second set of features;

where the classification circuit extracts a set of discriminative features from the ROI, where the set of discriminative features distinguishes the ROI represented in the diagnostic radiological image as a responder to immunosuppressive (IS) therapy or as a non-responder to IS therapy;

where the training circuit trains the classification circuit to identify a first member of the first set of features associated with response to IS therapy, or a second member of the first set of features associated with non-response to IS therapy, using the set of training radiological images; and where the CD prediction circuit generates a radiomic enterographic treatment (RET) score based, at least in part, on the diagnostic radiological image or the set of discriminative features.

16. The apparatus of claim 15, where the diagnostic radiological image or a member of the set of training radiological images is a gadolinium contrast-based magnetic resonance enterography (MRE) image of a region of tissue demonstrating CD pathology, where the diagnostic radiological image or the member of the set of training radiological images is acquired using a true fast imaging sequence with steady precession and fat suppression (TRUFIFS), a volumetric interpolated breath-hold examination (VIBE) sequence, or a half-Fourier acquisition single-shot turbo spin-echo (HASTE) sequence.

17. The apparatus of claim 15, where the classification circuit extracts the set of discriminative features from the ROI using a Wilcoxon rank sum test based on a five-fold cross-validation with 100 runs, where the set of discriminative features includes a gradient orientation feature based on a difference entropy of directionality, or a Gabor feature.

18. The apparatus of claim 15, where the CD prediction circuit generates the RET score by reducing the dimensionality of the set of discriminative features using principal component analysis (PCA) or spectral embedding (SE), where the RET score is a one-dimensional representation of a likelihood the region of tissue responds to IS therapy.

19. The apparatus of claim 15, where the first set of features or the second set of features includes at least ninety-five voxel-wise features, where the at least ninety-five voxel-wise features include a first order statistical feature, a second order statistical feature, an intensity feature, a Laws texture feature, a local binary pattern, a gradient orientation feature, a Haar wavelet, or a Gabor feature.

20. A method for planning delivery of immunosuppressive (IS) therapy, the method comprising:
accessing a magnetic resonance enterography (MRE) image of a region of tissue demonstrating Crohn's Disease (CD) pathology;
segmenting a region of interest (ROI) in the image from the background of the image;
generating a preprocessed ROI by removing intensity variations from the ROI;
extracting a first set of features from the preprocessed ROI, where the set of features includes a first order statistical feature, a second order statistical feature, an intensity feature, a Laws feature, a local binary pattern feature, a Haar wavelet, a gradient orientation feature, or a Gabor feature;

selecting a multi-dimensional subset of discriminative features from the first set of features, where the subset of discriminative features includes a gradient orientation feature;

computing a reduced-dimensionality personalized risk score using a principle component analysis (PCA) or spectral embedding (SE) of the multi-dimensional subset of discriminative features, where the reduced-dimensionality personalized risk score represents a probability that the ROI responds to IS therapy; and generating an IS therapy treatment plan based, at least in part, on the reduced-dimensionality personalized risk score.

* * * * *